United States Patent [19]

Fawcett et al.

[11] Patent Number: 4,759,764
[45] Date of Patent: Jul. 26, 1988

[54] PERIPHERAL NERVE REGENERATION

[75] Inventors: James W. Fawcett, San Diego, Calif.; Roger J. Keynes, Cambridge, England

[73] Assignee: Clayton Foundation for Research, Houston, Tex.

[21] Appl. No.: 80,232

[22] Filed: Jul. 28, 1987

Related U.S. Application Data

[63] Continuation of Ser. No. 738,086, May 24, 1985, abandoned.

[51] Int. Cl.$^4$ ............................................... A61F 2/02
[52] U.S. Cl. ........................................ 623/12; 623/66; 128/334 R
[58] Field of Search .................... 623/11, 12, 14, 66; 128/1 R, 334 R, 334 C, 346, 335.5; 435/1, 240, 241, 284, 285, 286

[56] References Cited

U.S. PATENT DOCUMENTS 3,551,560 12/1970 Thiele ................................. 623/66
4,662,884 5/1987 Stensaas ............................. 623/12

OTHER PUBLICATIONS

Jewett & McCarrol; *Nerve Repair & Regeneration Its Clinical & Experimental Basis;* "Chapter 25"; 1979 pp. 235-243.
Wallis, I., Koenig, E. and Rose, S. (1980) *Biochimica et Biophysica Acta,* 599, 505-517.
Wallis, I. and Koenig, E. (1980) *Biochimica et Biophysica Acta,* 599, 518-527.
Keynes, R. J., Hopkins, W. G. and Huang, C. L. H. (1984) *Brain Research,* 295, 275-281.
Ide, C., (1984), *Neuroscience Research,* 1, 379-391.
R. Madison et al., "Increased Rate of Peripheral Nerve Regeneration Using Bioresorbable Nerve Guides and a Laminin-Containing Gel," Exp. Neurol 88, 767-772 (1985).

*Primary Examiner*—Richard J. Apley
*Assistant Examiner*—Alan W. Cannon
*Attorney, Agent, or Firm*—Fulbright & Jaworski

[57] ABSTRACT

Basal lamina grafts for reconnecting severed nerves are prepared from muscle by removing cellular material therefrom while preserving the tubular structure of the basal lamina. When connected to nerve stumps the basal lamina surfaces promote axon regeneration therethrough, eventually reestablishing nerve function through the regenerated graft.

5 Claims, 1 Drawing Sheet

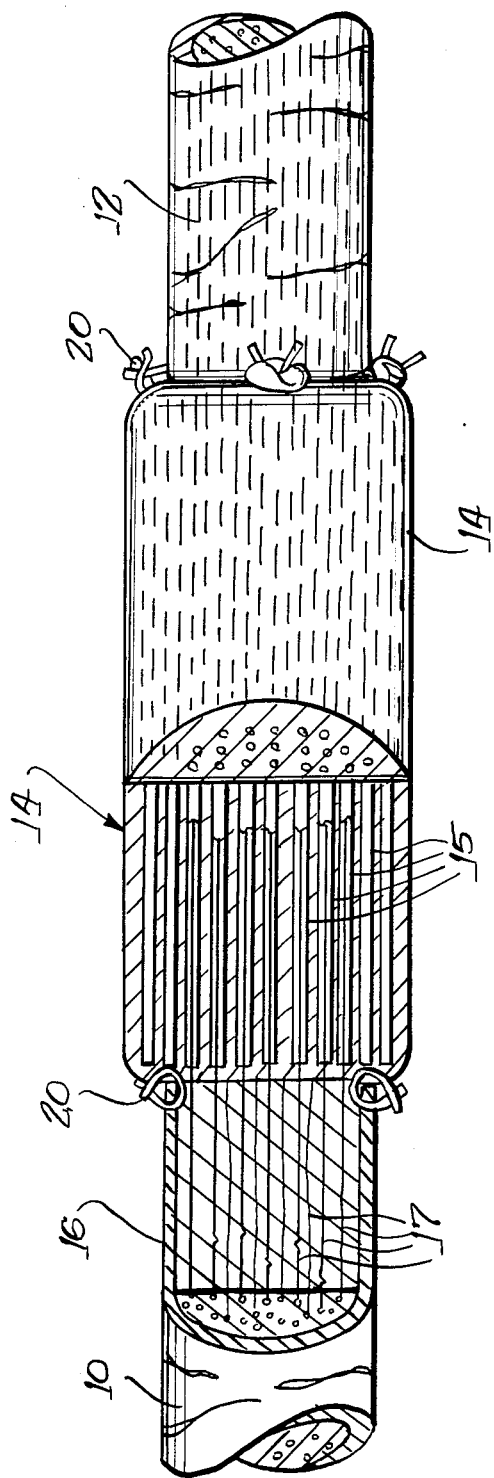

PERIPHERAL NERVE REGENERATION

This application is a continuation of application Ser. No. 738,086 filed May 24, 1985, now abandoned.

The present invention is directed to grafting of peripheral nerves, and more particularly to the use of basal lamina material as an intermediate graft between a proximal nerve stump and a distal nerve stump.

BACKGROUND OF THE INVENTION

An important surgical procedure, particularly in the case of trauma, is the restoration of peripheral nerve function. When a peripheral nerve is severed, the distal stump is unconnected to the central nervous system and cannot function. The severing of important peripheral nerves may seriously impair the function of appendages, and unless connection of the severed nerve is restored, the appendage is permanently disabled. For example, severing the radial, median or ulnar nerve of the arm will destroy to varying degrees the function of the arm and hand.

A nerve consists of a bundle of numerous fibers or axons through which the electrical signals that comprise nervous system impulses are transmitted. Surrounding the bundle of nerve fibers are Schwann cells which, in turn are surrounded by basal lamina, and additional connective tissue surrounds the whole nerve. In the case of a severed peripheral nerve in which the proximal and distal stumps can be approximated, rejoining of the nerve ends is generally accomplished by approximating the severed nerve ends and suturing their connective tissues together. In such cases, the regenerating axons can grow directly from the cut end of the proximal stump into the distal stump, and then on to their targets.

In many instances; however, the proximal and distal stumps may be separated by a distance which does not permit them to be directly approximated, necessitating the use of a shunt that promotes axon regeneration therethrough. One type of shunt may be a length of nerve obtained from another part of the body. For example, the sural nerve in humans is often cut to obtain a segment suitable for shunting a more important nerve elsewhere in a patient. The sural nerve is located in the leg and transmits sensations from the leg and foot, but does not transmit motor function impulses to the foot. Accordingly, it is felt desirable to use such a nerve to shunt more important motor function nerves, such as the radial, medial or ulnar nerves of the arm. Use of the sural nerve is desirably avoided because the loss of sensation occasioned by the severing thereof is of no mean consequence. Furthermore, removal of the sural nerve necessitates an operation of some consequence prior to the operation for restoring the severed nerve in which the removed sural nerve segment is to serve as a shunt.

It was discovered by Keynes et al. *Brain Research* 295 (1984), 275-281, that basal lamina of degenerating mammalian muscle provides surfaces which promote the regeneration of axons from the proximal stump of a severed nerve. It is believed that two substances, fibronectin and laminin, found in mammalian muscle basal lamina contribute to a conducive environment for axon regeneration. Thus, muscle specimens were obtained from mice and these tissue specimens were reimplanted into the mice, from which they were obtained, as a graft on the end of the proximal nerve stump, whereupon axon ingrowth into the tissue was observed. A problem with degenerating muscle tissue for use as a graft is its tendency to cause an intense inflammatory response in the host animal, including a human. This is particularly true if the specimen is not obtained from the same animal from which it was removed. Furthermore, if the cellular material cannot be removed by the body from within the basal lamina framework, it acts as a barrier to axon regeneration.

The need continues for improved grafts for connecting severed nerves, particularly for grafts that are generally useful for any recipient animal without serious potential of inducing an immune response.

SUMMARY OF THE INVENTION

A graft for joining a proximal stump of a peripheral nerve to a distal stump of a peripheral nerve comprises muscle basal lamina from which cellular material is substantially removed and in which the tubular structure of the basal lamina is substantially preserved. When used as a graft, the surfaces of the basal lamina tubes promote regeneration of axons therethrough, and the axon fibers ingrow into the distal stump which serves as a guide or conduit for further axon regeneration. To provide such a graft, muscle tissue is obtained from a living animal, and the cellular material is removed from the basal lamina tubes to provide a graft. To join a pair of nerve stumps together in a manner that promotes nerve fiber regeneration, the graft is attached to the proximal stump and to the distal stump with the basal lamina tubes extending longitudinally, substantially colinear with the nerve fibers.

IN THE DRAWINGS

The FIGURE is a perspective view, partially cut away, of a graft, prepared in accordance with the present invention, used as a graft to connect a proximal peripheral nerve stump and a distal peripheral nerve stump.

DETAILED DESCRIPTION OF THE PREFERRED EMBODIMENTS

In accordance with the present invention, it is found that muscle basal lamina from which cellular material has been removed provides an improved graft for joining a proximal peripheral nerve stump to a distal peripheral nerve stump. The graft is prepared by obtaining muscle tissue from a living animal and treating it to loosen cellular material from within the basal lamina tubes of the muscle tissue. Subsequently, the loosened cellular material is forced from the basal lamina tubes. In a surgical procedure using such a graft, the prepared graft is attached to the connective tissue surrounding the nerve fibers of both the proximal and distal stumps with the basal lamina tubes extending longitudinally, generally colinear with the stumps. The interior surfaces of the basal lamina tubes promote regeneration of axons from the proximal to the distal stump, and also the migration of Schwann cells, which myelinate the nerve fibers in the graft. The distal stump promotes further regeneration of the axons growing from the proximal stump, and this regeneration of fibers eventually leads to restoration of nerve function, i.e., transmission of nervous system signals.

Removal of the cellular material from the basal lamina tubes represents a significant improvement over the use of degenerating muscle tissues as a nerve graft. A major advantage of basal lamina tubes that are substantially free of cellular material is that the remaining tubular material has a very low capacity for inducing immune and inflammatory responses. It is found, in fact, that basal lamina tubes from which cellular material is removed can be obtained from one species and used in another species. In particular, muscle tissue obtained from rabbit and prepared in accordance with the present invention has been used as nerve grafts in rats without occurrence of serious immune-type rejection reactions and with subsequent regeneration of nerve axons through the basal lamina tubes.

That basal lamina material, substantially free of cellular material, can be used for cross-species transplants has important medical implications in that it may be possible to produce such grafts from another species, such as sheep muscles, and use the grafts prepared therefrom in human neurosurgery. In any case, the success of cross-species transplants indicates that there should be relatively little immune response generated by using prepared basal lamina tissue obtained from one animal of a species and implanted into another animal of the same species, e.g., tissue obtained from one human and implanted into another human. Thus a donor human, such as a donor human just killed in an accident, may serve as a source of graft tissue.

Another advantage of removing cellular material from basal lamina tubes is the removal of any physical impediment that the cellular material represents to axon ingrowth.

Removal of cellular material from muscle tissue to leave basal lamina tissue with substantially intact basal lamina tubes may be accomplished in a variety of ways. According to one general method, the muscle tissue recently obtained from a living animal (herein the donor "living animal" is intended to include immediately deceased or sacrificed animals, and the tissue from the living animal is used fresh or frozen) is exposed to a medium or a succession of media which tends to loosen the muscle cells from the basal lamina tubes. Subsequently, the cellular material is mechanically and osmotically forced from the tubes.

In one protocol, fresh muscle tissue is exposed first to a aqueous calcium chloride ($CaCl_2$) solution, 10 mMolar for a period of between 2 and 24 hours, next to a 30 mMolar potassium chloride (KCl) solution for between 12 and about 24 hours, and finally to a 0.09% triethanolamine buffer at pH 8.8 for between about 1 and about 6 hours. The low ionic strength of these solutions creates an osmotic pressure on the cells, tending to lyse the cells, and the osmotic pressure also helps to remove cellular material from the basal lamina tubes. Subsequent to treatment in the media, the cellular material is forced from the basal lamina tubes by mechanical pressure. In preliminary experiments, this is accomplished merely by pressing the media-treated tissue with a finger to force the cellular material therefrom. If grafts are to be prepared en masse, pressure will be applied in a more uniform and controllable manner, such as by passing the media-exposed tissue through rollers.

Another method of removing the cellular material is by freezing and thawing the muscle material repeatedly, preferably at least four times, in order to detach the cell membrane from the basal lamina. The disrupted cellular material is then forced from the basal lamina tubes by osmotic and/or mechanical force.

Although the above represent two suitable methods for removing cellular material from basal lamina tubes, it can be expected that a variety of treatments may be used to effect cellular material removal and at the same time leave the basal lamina tubular structure substantially intact. The graft, however, should function even if there is some break-down of the tubular structure because regenerating axons will cross between the tubes and continue growing toward the distal stump. While it would be desirable to remove cellular tissue entirely, some cellular material invariably remains within the tubes. Substantial removal of cellular material for purposes of the invention is the removal of at least about 75% by weight of the cellular material from the tissue specimen.

Basal lamina which is substantially free of cellular material has long term stability, and prepared grafts can be packaged and stored for use when needed. The prepared grafts may be stored frozen and then thawed at the time of use. Alternatively, the material may be packaged immersed in a sterile solution, such as a normal saline solution or a balanced salt solution, preferably with a small amount of antibiotics. Basal lamina material which is substantially free of cellular material inherently has a significantly longer shelf-life than does degenerating muscle tissue.

With reference to the FIGURE, a proximal nerve stump 10 is connected to a distal nerve stump 12 with a basal lamina graft 14 prepared in accordance with the present invention. The basal lamina graft 14 is prepared generally configured as a cylinder with its tubes 15 running longitudinally and with a diameter equal to or greater than the diameter of the connective tissue 16 surrounding the bundle 17 of nerve fibers. The graft, which may initially be prepared with a length greater than the distance between the stumps, so as to serve as a shunt to span a variety of gap lengths, is cut to size. Then the cylindrical graft 14 is secured with sutures 20 at the periphery of each of its ends to the connective tissue 16 of one of the nerve stumps, thereby connecting the stumps. Individual basal lamina tubes 15 run between the nerve bundles of each of the stumps. Being in close proximity to the proximal stump 10 and having surface components, such as fibronectin and laminin, which promote regeneration of axons, the nerve fibers begin to regenerate through the individual tubes, followed by migrating Schwann cells. Upon reaching the distal stump 12, the regenerating fibers continue to grow into the distal stump, eventually reestablishing at least partial nerve function.

Grafts prepared in accordance with the present invention may be used to span a gap between proximal and distal nerve stumps. Peripheral nerves of any thickness may be connected with such a graft of corresponding thickness. An important advantage of a basal lamina graft, relative to a segment of an actual nerve segment, is that the diameter of the artificial graft may be at least equal to the diameter of the nerve stumps. In cases where an important nerve that transmits motor function impulses is severed, available sensory nerves, such as the sural nerve, are typically smaller in diameter than the nerve stumps and, accordingly, several parallel lengths of sural nerve must be used to effect a repair. The quantity of suture material, and the extensive surgical manipulation needed to do this commonly results in considerable scar formation, which may prevent good axonal regeneration. By using basal lamina grafts prepared from muscle tissue, there is no problem in providing a graft of adequate diameter for promoting more complete recovery.

The invention will now be described by way of specific examples.

EXAMPLE 1

Basal lamina grafts were prepared from rabbit adductor magnus muscle. The rabbits were sacrificed, their adductor magnus muscles removed and cut into strips approximately 0.25 cm in diameter. The strips were placed in a 10 mM $CaCl_2$ solution for 2 hours at 4° C., transferred to a 30 mM KCl solution overnight at 4° C. and then transferred to a 0.09% triethylamine buffer, at pH 8.8 for two hours. Then, using a finger to press the strips against a hard surface, the cellular material or myoplasm was squeezed from the strips. The strips, useful as nerve grafts, were placed in Ringer's solution supplemented with penicillin and streptomycin to prevent bacterial or fungal growth. The grafts were stored at $-70°$ C. for up to 3 weeks.

EXAMPLE 2

Ten rabbits were anaesthized with nembutal (15-25 mg/Kg body weight, injected intravenously). In each, a 4 cm segment of the sciatic nerve was cut at both ends and removed. Then, a prepared graft strip was cut to corresponding length and sutured to each end of the severed nerve. After closing the incision, the rabbits were brought out of anaesthesia. Loss of function of the leg was observed, as a consequence of sciatic nerve function loss. After periods ranging from 20 to 40 days, however, the rabbits begin to exhibit functioning of the leg, indicating regeneration of the severed sciatic nerve.

After a period of 60 days, the rabbits were sacrificed. The grafts were removed and examined microscopically using standard staining and slicing techniques. This examination demonstrated nerve fiber growth through the graft, and into the distal stump of the severed nerve.

EXAMPLE 3

Using the grafts prepared in Example 1, the sciatic nerves of ten albino rats were severed and connected in the manner that the sciatic nerves of the rabbits were grafted in Example 2. The results were similar with initial loss of leg function gradually returning and with evidence of growth of axons into the grafts upon subsequent sacrifice of the rats. This experiment confirms the usefulness of the grafts prepared according to the present invention and further shows that the tissue can be used to repair nerves in species other than the species from which the graft basal lamina was derived.

Several advantages of the present invention can now be more fully appreciated. Basal lamina material free of cellular material has proven effective in reconnecting proximal and distal nerve stumps to act as a bridge for axonal regeneration, leading to a restoration of nerve impulse transmission. The substantial elimination of cellular material greatly reduces the chances of rejection of the graft by the receptor animal and the inflammation accompanying its implantation, as clearly demonstrated by the success of rabbit to rat grafts. The grafts are storable for extended periods of time, providing a readily available source of graft material. In cases where a surgeon believes that these grafts are appropriate, the necessity of using a patient's own nerve material for grafts is eliminated. Because the grafts can be formed of any required diameter, the grafts may actually provide better restoration of nerve function than nerve tissue itself.

While the invention has been described in terms of certain preferred embodiments, modifications obvious to one with ordinary skill in the art may be made without departing from the scope of the present invention. For example, although the invention has been described in terms of a graft in which the natural basal lamina tubular structure is substantially preserved, it may be possible to prepare an artificial structure using basal lamina material and being prepared to have a controlled porosity or microtubular structure that acts to guide axonal regeneration. Alternatively, basal lamina or the components thereof which promote axonal regeneration, might be used to impregnate a fibrous, synthetic, biocompatible material for use as a graft with the fibers serving to guide axon regeneration between the proximal and distal stumps.

Various features of the invention are set forth in the following Claims.

What is claimed:

1. A method for restoring nerve function of a severed peripheral nerve in a mammal of a first species which comprises joining the proximal stump of said severed nerve to a distal stump of said severed nerve by attaching to said stumps a graft, said graft comprising muscle basal lamina tubes from a mammal of a second species, which is the same as or different from said first species, the cellular material being substantially removed from said basal lamina tubes, and said basal lamina tubes extending longitudinally, substantially colinear with said stumps.

2. A method according to claim 1 wherein the graft is prepared by a process which comprises subjecting muscle tissue from a mammal to a medium or media which loosen cellular material from the basal lamina in the basal lamina tubes of the tissue and mechanically and/or osmotically forcing the loosened cellular material from the basal lamina tubes.

3. A method according to claim 1 wherein the graft is prepared by a process which comprises subjecting muscle tissue from a mammal to a repetitive freezing and thawing and, after said freezing and thawing, mechanically and/or osmotically forcing the loosened cellular material from the basal lamina tubes.

4. A method of claim 2 wherein the first species and second species are human.

5. A method of claim 3 wherein the first species and second species are human.

* * * * *